United States Patent
Imai (10) Patent No.: US 11,666,310 B2
(45) Date of Patent: Jun. 6, 2023

(54) ULTRASOUND DIAGNOSTIC APPARATUS AND METHOD FOR CONTROLLING ULTRASOUND DIAGNOSTIC APPARATUS USING PREDETERMINED IMAGING CONDITIONS FOR B-MODE IMAGE GENERATION

(71) Applicant: FUJIFILM Corporation, Tokyo (JP)

(72) Inventor: Yoshiro Imai, Ashigara-kami-gun (JP)

(73) Assignee: FUJIFILM Corporation, Tokyo (JP)

( * ) Notice: Subject to any disclaimer, the term of this patent is extended or adjusted under 35 U.S.C. 154(b) by 610 days.

(21) Appl. No.: 15/860,974

(22) Filed: Jan. 3, 2018

(65) Prior Publication Data

US 2018/0140281 A1    May 24, 2018

Related U.S. Application Data (63) Continuation of application No. PCT/JP2016/063833, filed on May 10, 2016.

(30) Foreign Application Priority Data

Aug. 21, 2015  (JP) .............................. JP2015-164173

(51) Int. Cl.
    *A61B 8/00*    (2006.01)
    *A61B 8/08*    (2006.01)
    *A61B 8/14*    (2006.01)

(52) U.S. Cl.
    CPC .............. *A61B 8/5207* (2013.01); *A61B 8/14* (2013.01); *A61B 8/54* (2013.01); *A61B 8/56* (2013.01);
    (Continued)

(58) Field of Classification Search
    CPC .... A61B 8/54; A61B 8/56; G06T 2207/10132
    See application file for complete search history.

(56) References Cited

U.S. PATENT DOCUMENTS

| 8,805,043 B1 * | 8/2014 | Suri | A61B 8/52 |
| | | | 382/131 |
| 2007/0049827 A1 * | 3/2007 | Donaldson | A61B 8/461 |
| | | | 600/443 |

(Continued)

FOREIGN PATENT DOCUMENTS

| EP | 1614386 A1 | 1/2006 |
| JP | 4-224738 A | 8/1992 |

(Continued)

OTHER PUBLICATIONS

Extended European Search Report, dated Jun. 12, 2018, for corresponding European Application No. 16838849.4.

(Continued)

*Primary Examiner* — Bill Thomson
*Assistant Examiner* — Amal Aly Farag
(74) *Attorney, Agent, or Firm* — Birch, Stewart, Kolasch & Birch, LLP (57) ABSTRACT

An ultrasound diagnostic apparatus includes an ultrasound probe and an imaging unit that transmits and receives an ultrasound beam to and from a subject using the ultrasound probe and converts a received signal output from the ultrasound probe into an image to generate an ultrasound image of the subject, according to set imaging conditions. The ultrasound diagnostic apparatus further includes a probe state determination unit that determines whether the ultrasound probe is in an aerial emission state or a contact state with the subject; and an apparatus control unit that changes the imaging conditions in a case in which the probe state determination unit determines that the ultrasound probe has been changed from the contact state with the subject to the aerial emission state and controls the imaging unit such that the ultrasound image is generated using the changed imaging conditions.

18 Claims, 7 Drawing Sheets

(52) U.S. Cl.
CPC ............... *A61B 8/463* (2013.01); *A61B 8/469* (2013.01); *G06T 2207/10132* (2013.01)

(56) References Cited

U.S. PATENT DOCUMENTS

| | | | |
|---|---|---|---|
| 2007/0112266 A1* | 5/2007 | Kishimoto | A61B 8/546 600/437 |
| 2008/0025583 A1* | 1/2008 | Jabri | G06T 7/0012 382/128 |
| 2009/0226062 A1* | 9/2009 | Nakamura | G06F 16/51 382/128 |
| 2009/0318809 A1* | 12/2009 | Okamura | A61B 8/14 600/443 |
| 2011/0166455 A1 | 7/2011 | Cully et al. | |
| 2015/0133786 A1* | 5/2015 | Wong | A61B 8/4427 600/441 |
| 2015/0320399 A1* | 11/2015 | Chono | A61B 8/486 382/131 |
| 2015/0335252 A1 | 11/2015 | Hirota | |

FOREIGN PATENT DOCUMENTS

| | | |
|---|---|---|
| JP | 2006-212146 A | 8/2006 |
| JP | 2014-180481 A | 9/2014 |
| JP | 2014-184025 A | 10/2014 |
| KR | 10-1437251 B1 | 9/2014 |

OTHER PUBLICATIONS

International Preliminary Report on Patentability and Written Opinion of the International Searching Authority (Forms PCT/IB/338, PCT/IB/373 and PCT/ISA/237) for Application No. PCT/JP2016/063833, dated Mar. 8, 2018, with an English translation.

International Search Report for International Application No. PCT/JP2016/063833, dated Jun. 21, 2016, with English translation.

* cited by examiner

ULTRASOUND DIAGNOSTIC APPARATUS AND METHOD FOR CONTROLLING ULTRASOUND DIAGNOSTIC APPARATUS USING PREDETERMINED IMAGING CONDITIONS FOR B-MODE IMAGE GENERATION

CROSS-REFERENCE TO RELATED APPLICATIONS

This application is a Continuation of PCT International Application No. PCT/JP2016/063833 filed on May 10, 2016, which claims priority under 35 U.S.C. § 119(a) to Japanese Patent Application No. 2015-164173 filed on Aug. 21, 2015. The above application is hereby expressly incorporated by reference, in its entirety, into the present application.

BACKGROUND OF THE INVENTION

1. Field of the Invention

The present invention relates to an ultrasound diagnostic apparatus and a method for controlling the ultrasound diagnostic apparatus, and more particularly, to an ultrasound diagnostic apparatus that performs the transmission and reception of an ultrasound beam and scanning according to predetermined imaging conditions and generates an ultrasound image.

2. Description of the Related Art

In the related art, an ultrasound diagnostic apparatus using an ultrasound image has been put to practical use in the medical field. In general, in this type of ultrasound diagnostic apparatus, an ultrasound probe provided with an array transducer scans a subject with an ultrasound beam and receives ultrasound echoes from the subject and the received signal is electrically processed to generate an ultrasound image.

In a case in which the ultrasound diagnostic apparatus is used to diagnose a plurality of imaging parts of the subject, appropriate imaging conditions vary depending on imaging parts in order to obtain ultrasound images suitable for diagnosis for each imaging part. Therefore, for example, JP1992-224738A (JP-H04-224738A) discloses an ultrasound diagnostic apparatus which automatically determines an imaging part from a generated ultrasound image, using a pattern matching process, and sets a scanning parameter most suitable for the imaging part on the basis of the determination result.

SUMMARY OF THE INVENTION

However, immediately after the imaging part is changed, an ultrasound image is generated under the imaging conditions corresponding to the imaging part immediately before the change. In a case in which there is a difference between the imaging conditions most suitable for the imaging part immediately before the change and the imaging conditions most suitable for the imaging part after the change, part determination needs to be performed using the ultrasound image of which the quality has been reduced since it has been generated under the imaging conditions unsuitable for the imaging part after the change. As a result, it is difficult to perform accurate part determination.

The invention has been made in order to solve the problems of the related art and an object of the invention is to provide an ultrasound diagnostic apparatus and a method for controlling the ultrasound diagnostic apparatus that can obtain an ultrasound image with stable quality regardless of an imaging part immediately before the imaging part is changed in a case in which the imaging part is changed.

An ultrasound diagnostic apparatus according to the invention comprises: an ultrasound probe; an imaging unit that transmits and receives an ultrasound beam to and from a subject using the ultrasound probe and converts a received signal output from the ultrasound probe into an image to generate an ultrasound image of the subject, according to set imaging conditions; a probe state determination unit that determines whether the ultrasound probe is in an aerial emission state or a contact state with the subject; and an apparatus control unit that changes the imaging conditions in a case in which the probe state determination unit determines that the ultrasound probe has been changed from the contact state with the subject to the aerial emission state and controls the imaging unit such that the ultrasound image is generated using the changed imaging conditions.

Preferably, the ultrasound diagnostic apparatus further comprises a part determination unit that determines an imaging part of the subject using the ultrasound image generated by the imaging unit. Preferably, the apparatus control unit controls the part determination unit such that part determination is not performed in a case in which the probe state determination unit determines that the ultrasound probe is in the aerial emission state and the part determination is performed in a case in which the probe state determination unit determines that the ultrasound probe has been changed from the aerial emission state to the contact state with the subject.

Preferably, the ultrasound diagnostic apparatus further comprises an imaging condition memory that stores a plurality of imaging conditions for each part which are set for each of a plurality of the imaging parts and imaging conditions for part determination which are common to the plurality of imaging parts. Preferably, the apparatus control unit controls the imaging unit such that the ultrasound image is generated using the imaging conditions for part determination stored in the imaging condition memory in a case in which the probe state determination unit determines that the ultrasound probe has been changed from the contact state with the subject to the aerial emission state, selects an imaging condition for each part corresponding to a determination result of the part determination unit from the plurality of imaging conditions for each part stored in the imaging condition memory in a case in which the part determination by the part determination unit has been completed, and controls the imaging unit such that the ultrasound image is generated using the selected imaging condition for each part.

The apparatus control unit may gradually change the imaging conditions from the imaging conditions for part determination to the selected imaging condition for each part in a case in which the part determination by the part determination unit has been completed.

The apparatus control unit may change the imaging conditions in a case in which the probe state determination unit determines that the ultrasound probe has been changed from the contact state with the subject to the aerial emission state and that the ultrasound probe is maintained in the aerial emission state for a predetermined set number of frames.

The ultrasound probe may include a motion sensor that detects an amount of movement of the ultrasound probe. The apparatus control unit may change the imaging conditions in a case in which the probe state determination unit determines that the ultrasound probe has been changed from the contact state with the subject to the aerial emission state and the amount of movement of the ultrasound probe detected by the motion sensor is equal to or greater than a predetermined threshold value.

The imaging unit may include a transmitting/receiving unit that transmits and receives the ultrasound beam according to ultrasound beam scanning conditions and an image generation unit that generates the ultrasound image from the received signal according to ultrasound image generation conditions. The imaging conditions may include the ultrasound beam scanning conditions and the ultrasound image generation conditions.

According to the invention, there is provided a method for controlling an ultrasound diagnostic apparatus including an ultrasound probe. The method comprises: a step of transmitting and receiving an ultrasound beam to and from a subject using the ultrasound probe and converting a received signal output from the ultrasound probe into an image to generate an ultrasound image of the subject, according to set imaging conditions; a step of determining whether the ultrasound probe is in an aerial emission state or a contact state with the subject; and a step of changing the imaging conditions in a case in which it is determined that the ultrasound probe has been changed from the contact state with the subject to the aerial emission state and generating the ultrasound image using the changed imaging conditions.

According to the invention, in a case in which it is determined that the ultrasound probe has been changed from the contact state with the subject to the aerial emission state, the imaging conditions are changed. In addition, the imaging unit is controlled such that the ultrasound image is generated under the changed imaging conditions. Therefore, in a case in which the imaging part is changed, it is possible to obtain an ultrasound image with stable quality, regardless of the imaging part immediately before the change.

DESCRIPTION OF THE PREFERRED EMBODIMENTS

Hereinafter, embodiments of the invention will be described with reference to the accompanying drawings.

Embodiment 1

Figure 1:
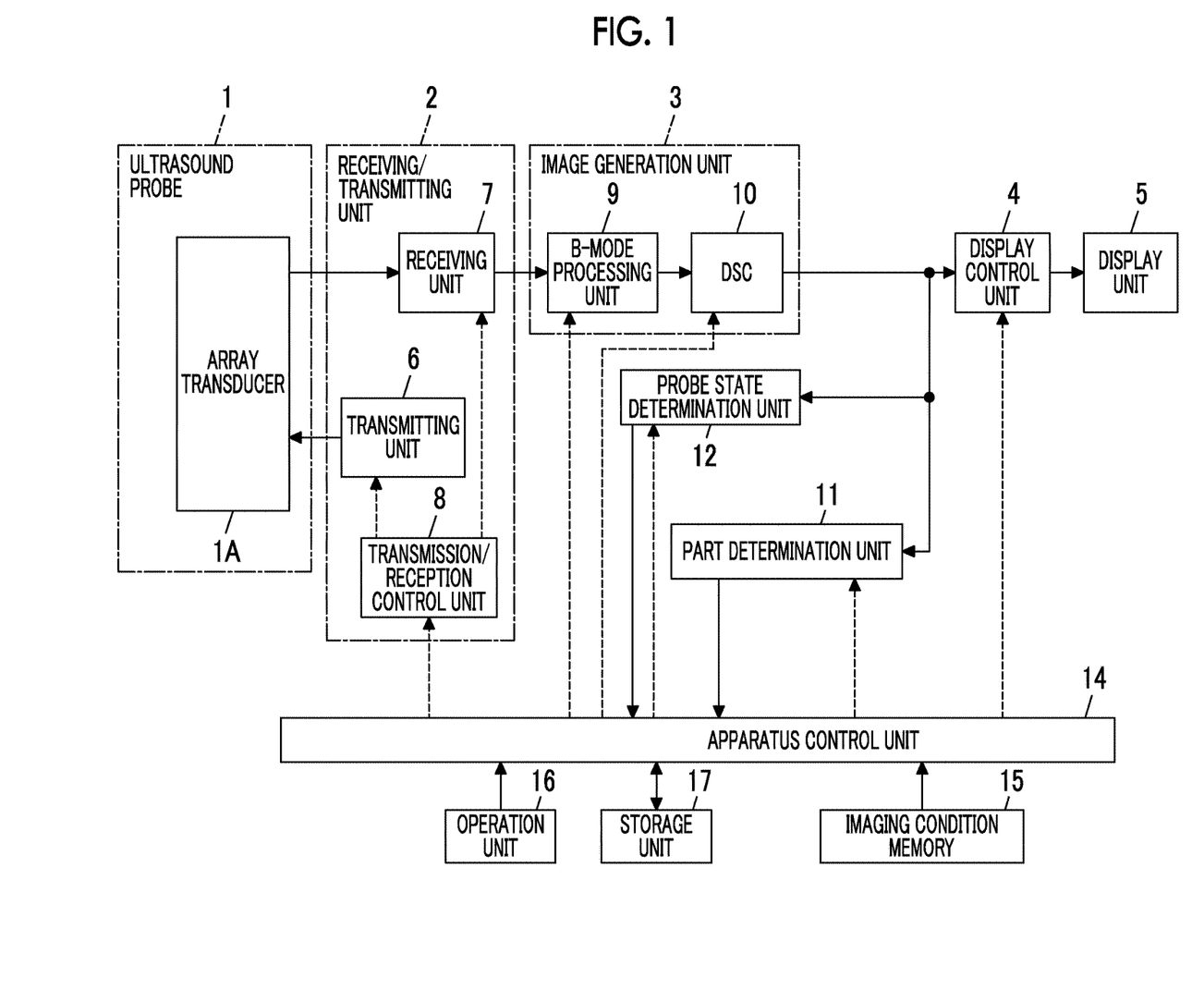
FIG. 1 is a block diagram illustrating the configuration of an ultrasound diagnostic apparatus according to Embodiment 1 of the invention.

FIG. 1 illustrates the configuration of an ultrasound diagnostic apparatus according to Embodiment 1 of the invention. The ultrasound diagnostic apparatus includes an ultrasound probe 1 provided with an array transducer 1A. An image generation unit 3 is connected to the ultrasound probe 1 through a transmitting/receiving unit 2 and a display unit 5 is connected to the image generation unit 3 through a display control unit 4.

The transmitting/receiving unit 2 includes a transmitting unit 6 and a receiving unit 7 that are connected to the array transducer 1A of the ultrasound probe 1 and a transmission/reception control unit 8 that is connected to the transmitting unit 6 and the receiving unit 7. The image generation unit 3 includes a B-mode processing unit 9 that is connected to the receiving unit 7 of the transmitting/receiving unit 2 and a digital scan converter (DSC) 10 that is connected to the B-mode processing unit 9. The display control unit 4 is connected to the DSC 10.

In addition, a part determination unit 11 and a probe state determination unit 12 are connected to the DSC 10 of the image generation unit 3.

An apparatus control unit 14 is connected to the transmission/reception control unit 8 of the transmitting/receiving unit 2, the B-mode processing unit 9 and the DSC 10 of the image generation unit 3, the display control unit 4, the part determination unit 11, and the probe state determination unit 12. In addition, an imaging condition memory 15, an operation unit 16, and a storage unit 17 are connected to the apparatus control unit 14.

The array transducer 1A of the ultrasound probe 1 includes a plurality of ultrasound transducers that are one-dimensionally or two-dimensionally arranged. Each of the ultrasound transducers transmits ultrasonic waves in response to a driving signal supplied from the transmitting unit 6. In addition, each of the ultrasound transducers receives ultrasound echoes from a subject and outputs a received signal. Each ultrasound transducer is, for example, a transducer in which electrodes are formed on both sides of a piezoelectric body made of piezoelectric ceramic typified by lead zirconate titanate (PZT), a polymer piezoelectric element typified by polyvinylidene difluoride (PVDF), or piezoelectric single crystal typified by lead magnesium niobate-lead titanate (PMN-PT).

In a case in which a pulsed voltage or a continuous-wave voltage is applied to the electrodes of the transducer, the piezoelectric body is expanded and contracted and pulsed or continuous ultrasonic waves are generated from each transducer. The ultrasonic waves are combined to form an ultrasound beam. In addition, each transducer receives propagated ultrasonic waves, is expanded and contracted, and generates an electric signal. The electric signal is output as a received ultrasound signal.

The transmitting/receiving unit 2 transmits and receives an ultrasound beam according to the set ultrasound beam scanning conditions and the image generation unit 3 generates a B-mode image signal according to the set ultrasound image generation conditions. Therefore, the transmitting/receiving unit 2 and the image generation unit 3 form an imaging unit. In addition, imaging conditions for the imaging unit include the ultrasound beam scanning conditions for the transmitting/receiving unit 2 and the ultrasound image generation conditions for the image generation unit 3.

Among the imaging conditions, the ultrasound beam scanning conditions can include an ultrasound beam transmission frequency, a focal position, and a display depth and the ultrasound image generation conditions can include a sound speed, detection conditions, a gain, a dynamic range, a gradation curve, speckle reduction intensity, and the degree of edge enhancement.

The transmitting unit 6 of the transmitting/receiving unit 2 includes, for example, a plurality of pulse generators, adjusts the amount of delay of each driving signal such that the ultrasonic waves transmitted from a plurality of ultrasound transducers in the array transducer 1A form an ultrasound beam, on the basis of a transmission delay pattern selected according to a control signal from the transmission/reception control unit 8, and supplies the driving signals to the plurality of ultrasound transducers.

Figure 2:
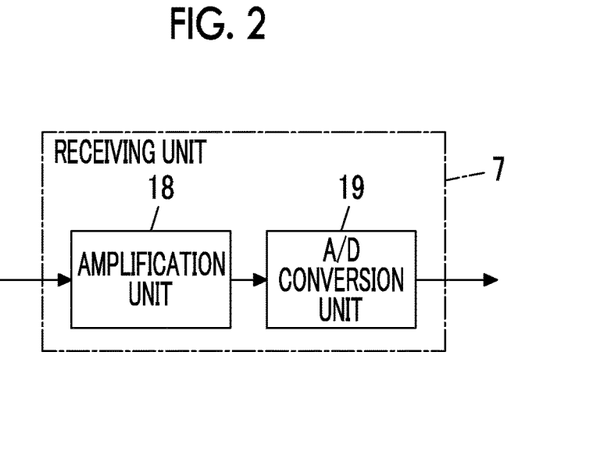
FIG. 2 is a block diagram illustrating the internal configuration of a receiving unit.

As illustrated in FIG. 2, the receiving unit 7 has a configuration in which an amplification unit 18 and an analog/digital (A/D) conversion unit 19 are sequentially connected in series. The receiving unit 7 amplifies the received signals transmitted from each ultrasound transducer of the array transducer 1A with the amplification unit 18 and performs A/D conversion for the received signals with the A/D conversion unit 19 to generate digital received data.

The transmission/reception control unit 8 controls the transmitting unit 6 and the receiving unit 7 on the basis of various control signals transmitted from the apparatus control unit 14 such that the transmission of an ultrasound pulse to a subject and the reception of an ultrasound echo from the subject are repeated at a pulse repetition frequency (PRF) interval.

Figure 3:
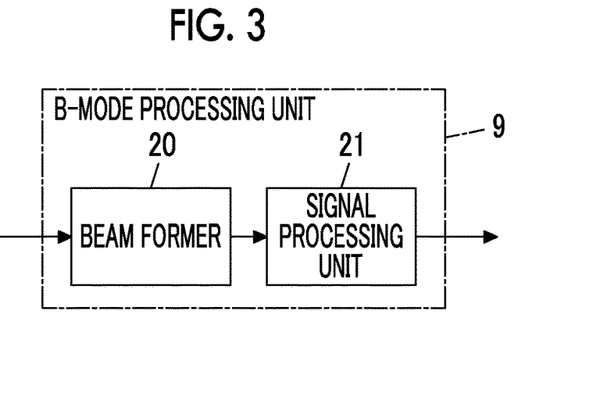
FIG. 3 is a block diagram illustrating the internal configuration of a B-mode processing unit.

The B-mode processing unit 9 of the image generation unit 3 has a configuration in which a beam former 20 and a signal processing unit 21 are sequentially connected in series, as illustrated in FIG. 3. The beam former 20 applies a delay to each received data item output from the receiving unit 7 of the transmitting/receiving unit 2 according to a sound speed or a sound speed distribution set on the basis of a reception delay pattern selected according to a control signal from the apparatus control unit 14 and adds the received data to perform a reception focusing process. A sound ray signal in which the focus of an ultrasound echo subjected to phasing addition is narrowed is generated by the reception focusing process.

The signal processing unit 21 corrects the attenuation of the sound ray signal generated by the beam former 20 depending on a distance according to the depth of the reflection position of ultrasonic waves and then performs an envelope detection process. In addition, the signal processing unit 21 performs various types of necessary image processing including a gradation process to generate a B-mode image signal which is tomographic image information about the issues of the subject.

The DSC 10 of the image generation unit 3 converts the B-mode image signal generated by the signal processing unit 21 into an image signal based on a general television signal scanning system (raster conversion).

The display control unit 4 displays a B-mode image on the display unit 5 on the basis of the B-mode image signal generated by the image generation unit 3.

The display unit 5 includes a display device, such as a liquid crystal display (LCD), and displays the B-mode image under the control of the display control unit 4.

The part determination unit 11 determines an imaging part of the subject on the basis of the B-mode image signal generated by the image generation unit 3.

The probe state determination unit 12 determines whether the ultrasound probe 1 is in a contact state in which the ultrasound probe 1 comes into contact with the body surface of a subject and emits ultrasonic waves into the body of the subject or an aerial emission state in which the ultrasound probe 1 is separated from the body surface of the subject and emits ultrasonic waves to the air, on the basis of the B-mode image generated by the image generation unit 3.

The apparatus control unit 14 controls the transmission/reception control unit 8, the B-mode processing unit 9, the DSC 10, the display control unit 4, the part determination unit 11, and the probe state determination unit 12 on the basis of commands input by the operator through the operation unit 16.

The imaging condition memory 15 stores a plurality of imaging conditions for each part which are set for a plurality of imaging parts of the subject and imaging conditions for part determination which are common to a plurality of imaging parts of the subject in advance. The plurality of imaging conditions for each part are used to acquire a B-mode image suitable for diagnosing each corresponding imaging part. In contrast, the imaging conditions for part determination do not correspond to a specific imaging part, are common to all of the imaging parts, and are used to acquire a B-mode image for accurate part determination.

The operation unit 16 is used by the operator to perform an input operation and may include, for example, a keyboard, a mouse, a trackball, and a touch panel.

The storage unit 17 stores, for example, an operation program. For example, a recording medium, such as a hard disk, a flexible disk, an MO, an MT, a RAM, a CD-ROM, a DVD-ROM, an SD card, a CF card, or a USB memory, or a server may be used as the storage unit 17.

Here, a part determination method in the part determination unit 11 will be described.

Examples of the imaging part of the subject can include the heart, the right abdomen, the left abdomen, and the urinary bladder. Of course, the part determination unit 11 may be configured so as to determine various other imaging parts.

The part determination unit 11 stores the typical pattern data of a plurality of imaging parts in advance and calculates the similarity between the B-mode image signal of the imaging part output from the DSC 10 of the image generation unit 3 and each of a plurality of pattern data items stored in advance. A known matching technique can be used to calculate the similarity. In addition to the matching technique, for example, the following method may be used to calculate the similarity: a machine learning method disclosed in Csurka et al.: Visual Categorization with Bags of Keypoints, Proc. of ECCV Workshop on Statistical Learning in Computer Vision, pp. 59-74 (2004); or a general image recognition method using deep learning disclosed in Krizhevsk et al.: ImageNet Classification with Deep Convolutional Neural Networks, Advances in Neural Information Processing Systems 25, pp. 1106-1114 (2012).

The part determination unit 11 calculates similarity scores between the B-mode image signal of the imaging part and a plurality of imaging parts, using these methods, and uses an imaging part with the highest similarity score as the determination result. For example, in a case in which the similarity score for the heart is 5, the similarity score for the right abdomen is 10, the similarity score for the left abdomen is 6, and the similarity score for the urinary bladder is 3, the determination result indicating that the captured imaging part is the right abdomen with the highest similarity score is obtained.

In this case, the following configuration may be used: before the part is determined, the operator inputs subject information (for example, a body type and sex) through the operation unit 16 and pattern data used to determine the part is changed according to the subject information. That is, a plurality of pattern data items corresponding to, for example, a difference in body size and sex are stored for each imaging part and the part is determined on the basis of pattern data corresponding to the input subject information. With this configuration, it is possible to prevent an error in determination caused by the difference in the body size and sex of the subject and to improve the accuracy of determining the part.

The determination of the part by the part determination unit 11 may be performed for each display frame of the B-mode image or may be performed for every several frames for one imaging part.

Figure 4:
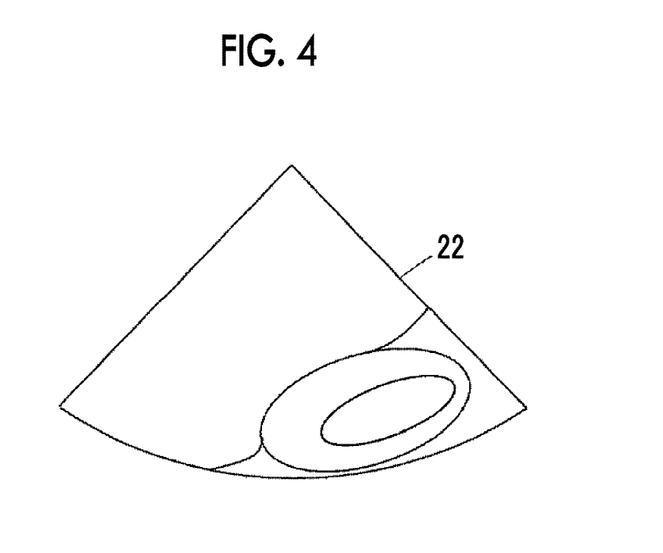
FIG. 4 is a diagram illustrating a B-mode image in Embodiment 1.

In this embodiment, the probe state determination unit 12 determines whether the ultrasound probe 1 is in the contact state with the subject or the aerial emission state. However, the probe state determination unit 12 may analyze the B-mode image generated by the image generation unit 3 to perform the determination. In general, in a case in which the ultrasound probe 1 comes into contact with the body surface of the subject and emits ultrasonic waves into the body of the subject, a certain structure, that is, a tissue of the subject is visualized in a B-mode image 22 as illustrated in FIG. 4. However, in a case in which the ultrasound probe 1 is separated from the body surface of the subject and emits ultrasonic waves to the air, no structure is visualized in the B-mode image 22.

Therefore, it is detected whether a structure is present or absent in the B-mode image 22 on the basis of a brightness distribution of the B-mode image 22. In a case in which a structure is detected in the B-mode image 22, it can be determined that the ultrasound probe 1 is in the contact state with the subject. In a case in which no structure is detected in the B-mode image 22, it can be determined that the ultrasound probe 1 is in the aerial emission state.

Figure 5:
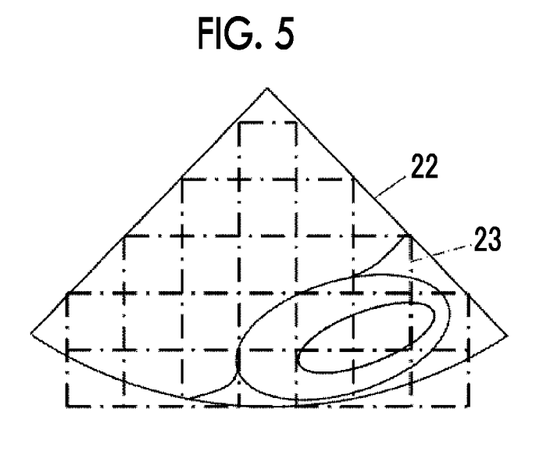
FIG. 5 is a diagram illustrating a B-mode image in which a plurality of regions of interest are set.

Specifically, as illustrated in FIG. 5, the B-mode image 22 is divided into a plurality of regions 23. The variance of the brightness of each region 23 or the difference between the maximum brightness and the minimum brightness is calculated as an index value. In a case in which the number of regions 23 with an index value that is equal to or greater than a predetermined set value is equal to or greater than a predetermined threshold value, the probe state determination unit 12 determines that the ultrasound probe 1 is in the contact state with the subject. On the other hand, in a case in which the number of regions 23 with an index value that is equal to or greater than the predetermined set value is less than the predetermined threshold value, the probe state determination unit 12 determines that the ultrasound probe 1 is in the aerial emission state.

Figure 6:
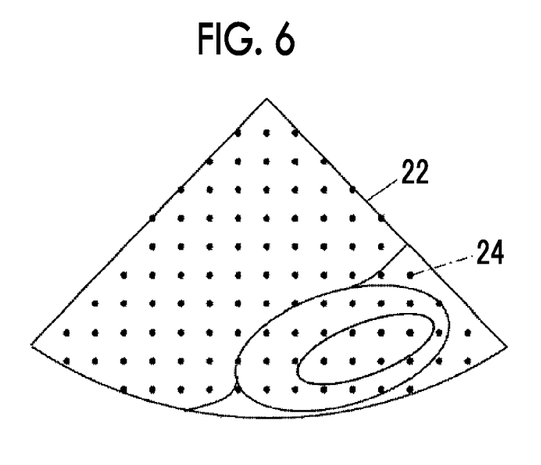
FIG. 6 is a diagram illustrating a B-mode image in which a plurality of observation points are set.

In addition to the analysis based on the index value of the brightness of each region 23, a plurality of observation points 24 may be set in the B-mode image 22 as illustrated in FIG. 6 and the amount of movement of each observation point 24 between frames may be detected to determine the state of the ultrasound probe 1.

In a case in which the number of observation points 24 of which the amount of movement between frames is equal to or less than a set value is equal to or greater than a predetermined threshold value, the probe state determination unit 12 may determine that the movement of the ultrasound probe 1 is stable and may determine whether the ultrasound probe 1 is in the contact state with the subject or the aerial emission state on the basis of the index value of the brightness of each region 23.

In a case in which the ultrasound probe 1 is in the aerial emission state, it is considered that almost the same B-mode image is acquired. Therefore, the B-mode image in a case in which the ultrasound probe 1 is in the aerial emission state may be stored in advance and the probe state determination unit 12 may determine the state of the ultrasound probe 1, using a matching technique such as template matching.

The apparatus control unit 14 controls whether to perform part determination using the part determination unit 11, on the basis of the determination result of the state of the ultrasound probe 1 by the probe state determination unit 12. That is, in a case in which the probe state determination unit 12 determines that the ultrasound probe 1 is in the aerial emission state, the apparatus control unit 14 does not perform part determination. In a case in which the probe state determination unit 12 determines that the ultrasound probe 1 has been changed from the aerial emission state to the contact state with the subject, the apparatus control unit 14 controls the part determination unit 11 such that part determination is performed.

The imaging conditions for part determination stored in the imaging condition memory 15 include, for example, at least one of the following set conditions.

(1) Image Gain

The average brightness of each region 23 or the average brightness of the entire screen is set so as to fall within a given target range predetermined in the ultrasound diagnostic apparatus, using the result of image analysis by the probe state determination unit 12. For example, the average brightness of the regions 23 or the average brightness of the entire screen is set between the maximum value of brightness that is 10% less than the maximum brightness predetermined in the ultrasound diagnostic apparatus and the minimum value of brightness that is 10% greater than the minimum brightness predetermined in the ultrasound diagnostic apparatus.

(2) Image Dynamic Range

The average brightness of each region 23, the average brightness of the entire screen, or the dynamic range of the entire screen is set so as to fall within a given target range predetermined in the ultrasound diagnostic apparatus, using the result of image analysis by the probe state determination unit 12.

(3) Gradation Curve

A gradation curve is set such that a specific gradation range is not highlighted.

(4) Degree of Sharpness Enhancement, Degree of Speckle Reduction, and Degree of Edge Enhancement The degree of sharpness enhancement, the degree of speckle reduction, and the degree of edge enhancement are set to 0 (no enhancement is performed).

(5) Display Depth of Image

The display depth of an image is set to an intermediate value of the maximum depth.

(6) Focal Position of Image

The focal position of an image is set to the middle of the display depth of the image.

(7) Image Transmission Frequency

The image transmission frequency is set to an intermediate frequency of the transmission band of the array transducer 1A of the ultrasound probe 1.

Figure 7:
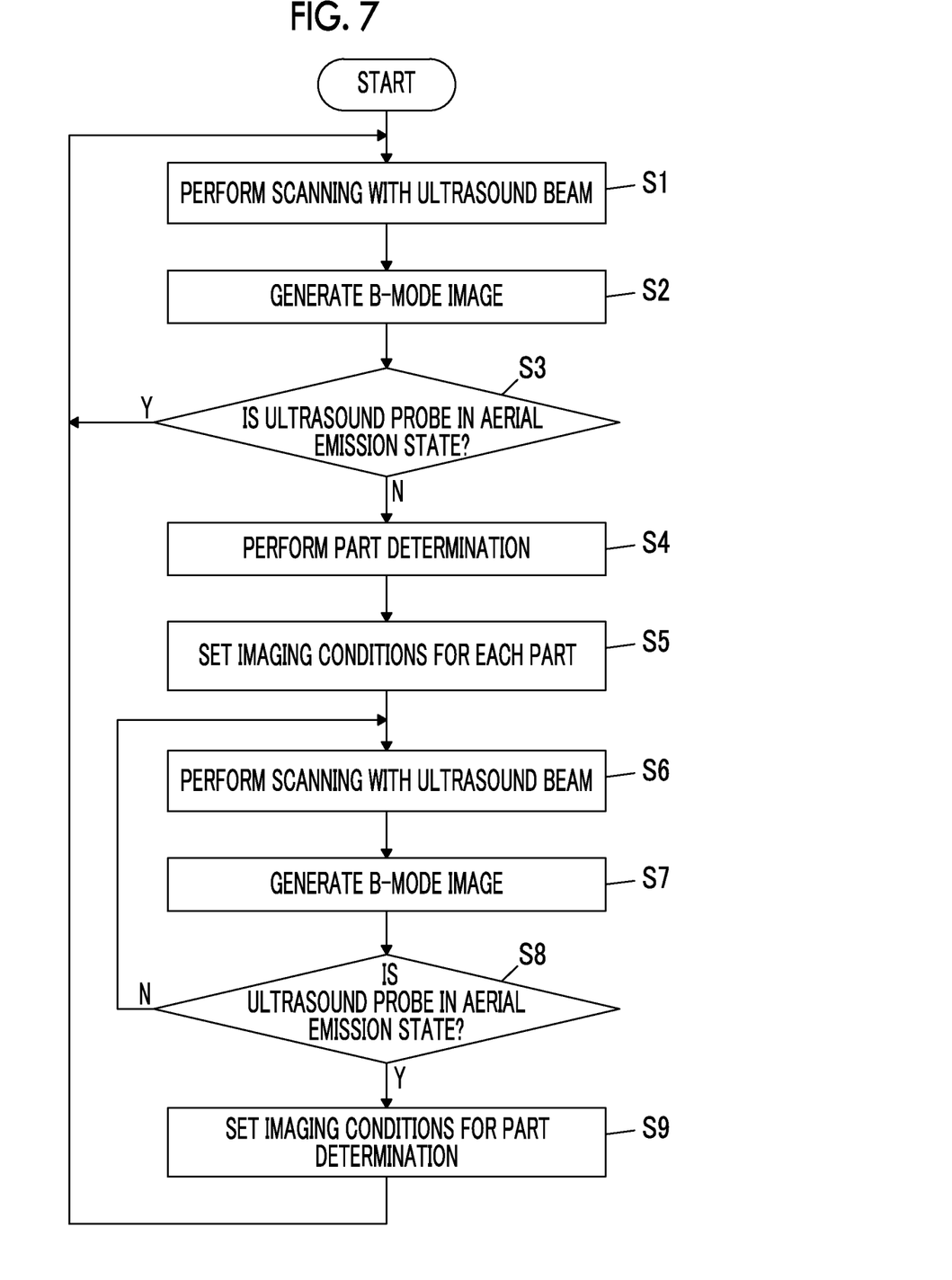
FIG. 7 is a flowchart illustrating the operation of Embodiment 1.

Next, the operation of Embodiment 1 will be described with reference to the flowchart illustrated in FIG. 7.

It is assumed that, as initial settings, the apparatus control unit 14 selects the imaging conditions for part determination which have been stored in the imaging condition memory 15 in advance and controls the transmitting/receiving unit 2 and the image generation unit 3 such that imaging is performed according to the imaging conditions for part determination.

First, in Step S1, the transmitting/receiving unit 2 performs the transmission and reception of an ultrasound beam and scanning, using the plurality of ultrasound transducers in the array transducer 1 A of the ultrasound probe 1. A received signal from each ultrasound transducer that has received ultrasound echoes from the subject is output to the receiving unit 7. The receiving unit 7 performs amplification and A/D conversion for the received signal to generate received data.

In Step S2, the received data is input to the image generation unit 3. The B-mode processing unit 9 performs the reception focusing process for the received data and the DSC 10 converts signal conversion to generate a B-mode image signal. The B-mode image signal is output from the image generation unit 3 to the display control unit 4. The B-mode image is displayed on the display unit 5.

The B-mode image signal output from the DSC 10 of the image generation unit 3 is input to the part determination unit 11 and the probe state determination unit 12. In Step S3, the probe state determination unit 12 determines whether the ultrasound probe 1 is in the contact state with the subject or the aerial emission state.

In a case in which it is determined in Step S3 that the ultrasound probe 1 is not in the aerial emission state, but is in the contact state in which the ultrasound probe 1 comes into contact with the body surface of the subject, in Step S4, the part determination unit 11 performs part determination and the determination result is output from the part determination unit 11 to the apparatus control unit 14. In this case, the imaging conditions for part determination selected as the initial settings do not correspond to a specific imaging part and are common to all of the imaging parts. Imaging is performed according to the imaging conditions for part determination. Therefore, it is possible to stably acquire a B-mode image, regardless of the imaging part. In Step S4, the part determination unit 11 can perform part determination with high accuracy.

Then, in Step S5, the apparatus control unit 14 sets the imaging conditions for each part corresponding to the determination result of the part determination unit 11. The apparatus control unit 14 selects an imaging condition for each part corresponding to the determination result from a plurality of imaging conditions for each part which have been stored in the imaging condition memory 15 in advance, on the basis of the determination result input from the part determination unit 11 and controls the transmitting/receiving unit 2 and the image generation unit 3 such that imaging is performed on the basis of the selected imaging condition for each part.

As such, in a state in which the imaging condition for each part corresponding to the determination result of the part determination unit 11 is set, imaging is performed in Steps S6 and S7. That is, in Step S6, the transmission and reception of an ultrasound beam and scanning are performed according to the ultrasound beam scanning condition included in the imaging condition for each part selected from the imaging condition memory 15. In Step S7, a B-mode image signal is generated from the received signal according to the ultrasound image generation condition included in the selected imaging condition for each part and a B-mode image is displayed on the display unit 5.

The imaging process in Steps S6 and S7 is continuously performed until it is determined that the ultrasound probe 1 has been changed from the contact state with the subject to the aerial emission state in Step S8. In this way, the imaging part is examined.

Then, in a case in which the probe state determination unit 12 determines that the ultrasound probe 1 has been changed from the contact state with the subject to the aerial emission state in Step S8, the process proceeds to Step S9 and the apparatus control unit 14 sets the imaging conditions for part determination. That is, since the ultrasound probe 1 has been changed from the contact state with the subject to the aerial emission state, the apparatus control unit 14 determines that the imaging part has been changed, selects the imaging conditions for part determination stored in the imaging condition memory 15 in advance, and controls the transmitting/receiving unit 2 and the image generation unit 3 such that imaging is performed under the selected imaging conditions for part determination.

As such, in a state in which the imaging conditions for part determination are set, the process returns to Step S1. In Steps S1 and S2, imaging is performed. Then, in a case in which it is determined in Step S3 that the ultrasound probe 1 has been changed from the aerial emission state to the contact state with the subject, the process proceeds to Step S4 and the part determination unit 11 performs part determination.

In Step S9, the imaging conditions for each part are changed to the imaging conditions for part determination. Then, imaging is performed in Steps S1 and S2. Therefore, the B-mode image used for part determination in Step S4 has stable quality regardless of a new imaging part. As a result, the part determination unit 11 can perform part determination with high accuracy.

In this way, whenever the probe state determination unit 12 determines that the ultrasound probe 1 has been changed from the contact state with the subject to the aerial emission state, the imaging conditions for part determination are set and the part determination unit 11 performs part determination on the basis of the B-mode image generated according to the imaging conditions for part determination. Therefore, in a case in which the imaging part is changed, it is possible to obtain an ultrasound image with stable quality, regardless of the imaging part immediately before the change, and to perform accurate part determination.

The imaging conditions for part determination set by the apparatus control unit 14 in Step S9 may be adjusted according to a part determination method in the part determination unit 11. For example, in a case in which matching for calculating the similarity is performed at low resolution, it is preferable that the conditions that have a great effect on the brightness and gradation of an image, such as a gain and a dynamic range, are changed from the imaging conditions for each part to conditions common to all of the imaging parts. The conditions that have a small effect on the brightness and gradation of an image, such as the degree of sharpness enhancement or the degree of speckle reduction, may not be changed and the conditions included in each imaging condition for each part may be used without any change.

Inversely, in a case in which matching is performed using, for example, a texture feature amount, it is preferable to change the degree of sharpness enhancement and the degree of speckle reduction from the imaging conditions for each part to conditions common to all of the imaging parts.

In a case in which the imaging conditions for each part are set on the basis of the determination result output from the part determination unit 11 in Step S5 after the determination of the part by the part determination unit 11 is completed in Step S4, the imaging conditions for part determination during part determination may not be immediately changed to the imaging conditions for each part, but may be gradually changed for a plurality of frames.

For example, in a case in which the value of the gain in the imaging conditions for part determination used during part determination is "60" and the value of the gain in the imaging conditions for each part set after part determination is "80", the value of the gain for each frame is increased by "4" for five frames to gradually change the imaging conditions from the imaging conditions for part determination to the imaging conditions for each part.

With this configuration, it is possible to smoothly change image quality from a B-mode image for part determination to a B-mode image for examining the imaging part and to reduce a sense of discomfort caused by a rapid change in image quality.

Embodiment 2

In the above-described Embodiment 1, in a case in which the probe state determination unit 12 determines that the ultrasound probe 1 has been changed from the contact state with the subject to the aerial emission state in Step S8, the process immediately proceeds to Step S9 and the imaging conditions for part determination are set. However, the invention is not limited thereto.

Figure 8:
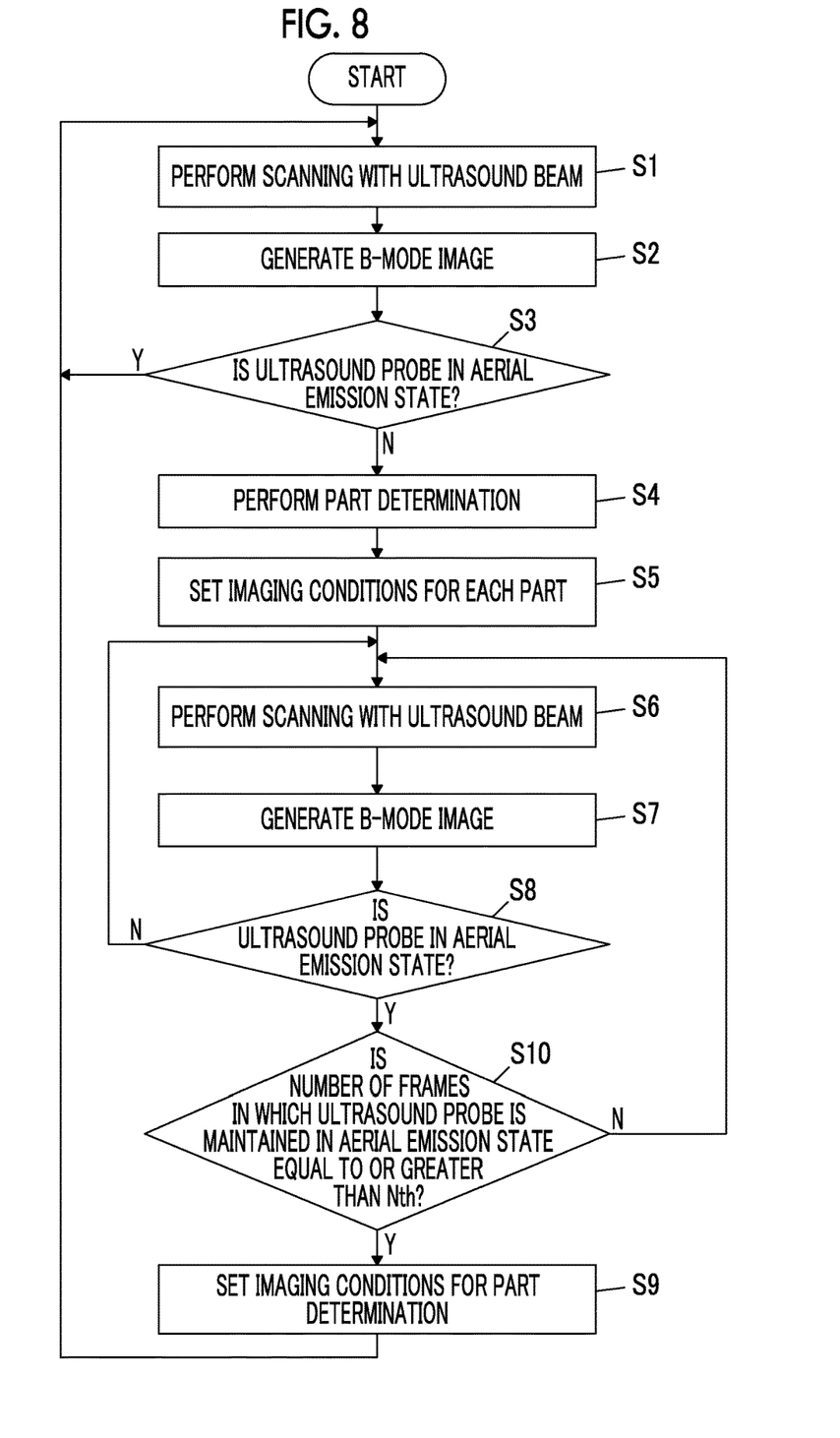
FIG. 8 is a flowchart illustrating the operation of Embodiment 2.

For example, as illustrated in FIG. 8, in a case in which the probe state determination unit 12 determines that the ultrasound probe 1 is maintained in the aerial emission state for a predetermined set number of frames Nth in Step S10 after the probe state determination unit 12 determines that the ultrasound probe 1 has been changed from the contact state with the subject to the aerial emission state in Step S8, the process may proceed to Step S9 and the imaging conditions for part determination may be set.

In a case in which the ultrasound probe 1 is maintained in the aerial emission state for the set number of frames Nth, the apparatus control unit 14 determines that the operator has separated the ultrasound probe 1 from the body surface of the subject in order to change the imaging part and sets the imaging conditions for part determination. On the other hand, in a case in which the ultrasound probe 1 is maintained in the aerial emission state for only the frames whose number is less than the set number Nth and then returned to the contact state with the subject, the apparatus control unit 14 determines that the operator has instantaneously separated and lifted the ultrasound probe 1 from the body surface of the subject, without intention, during an imaging operation for the imaging part, and uses the set imaging conditions for each part, without any change.

With this configuration, it is possible to reliably recognize that the ultrasound probe 1 has been changed to the aerial emission state in order to change the imaging part and to set the imaging conditions for part determination.

In addition, the number of frames may be directly set. For example, the set number Nth may be set to, for example, "90". Alternatively, the following configuration may be used: the operator input a time of, for example, "3 seconds" and the time is automatically converted into the number of frames according to a frame rate.

Embodiment 3

Figure 9:
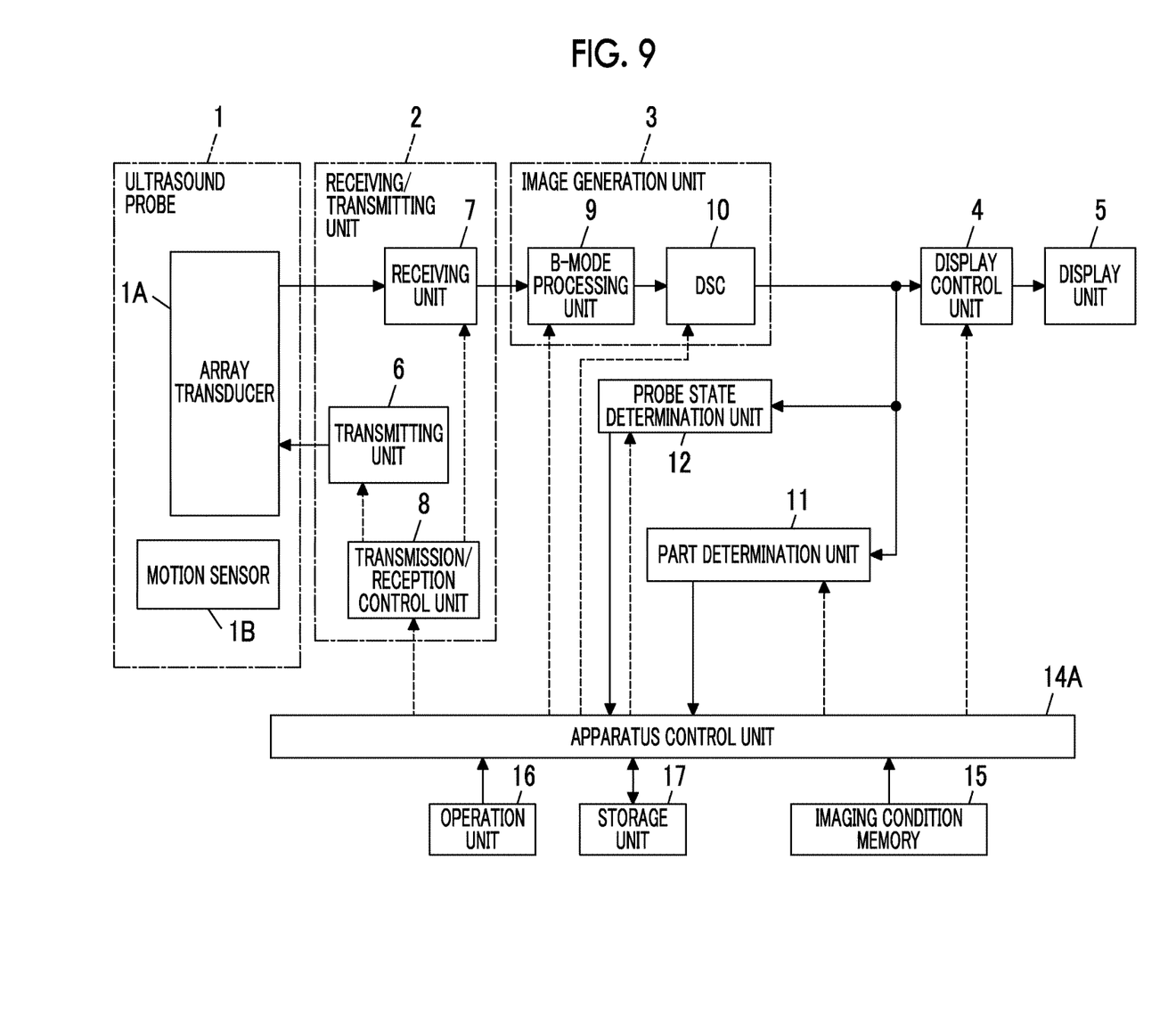
FIG. 9 is a block diagram illustrating the configuration of an ultrasound diagnostic apparatus according to Embodiment 3.

FIG. 9 illustrates the configuration of an ultrasound diagnostic apparatus according to Embodiment 3. The ultrasound diagnostic apparatus differs from the ultrasound diagnostic apparatus according to Embodiment 1 illustrated in FIG. 1 in that the ultrasound probe 1 includes a motion sensor 1B and an apparatus control unit 14A is used instead of the apparatus control unit 14.

The motion sensor 1B detects the amount of movement of the ultrasound probe 1. Specifically, the motion sensor 1B is, for example, an acceleration sensor or a posture sensor.

The apparatus control unit 14A sets the imaging conditions for part determination in a case in which the probe state determination unit 12 determines that the ultrasound probe 1 has been changed from the contact state with the subject to the aerial emission state and the amount of movement of the ultrasound probe 1 detected by the motion sensor 1B is equal to or greater than a predetermined threshold value Mth.

Figure 10:
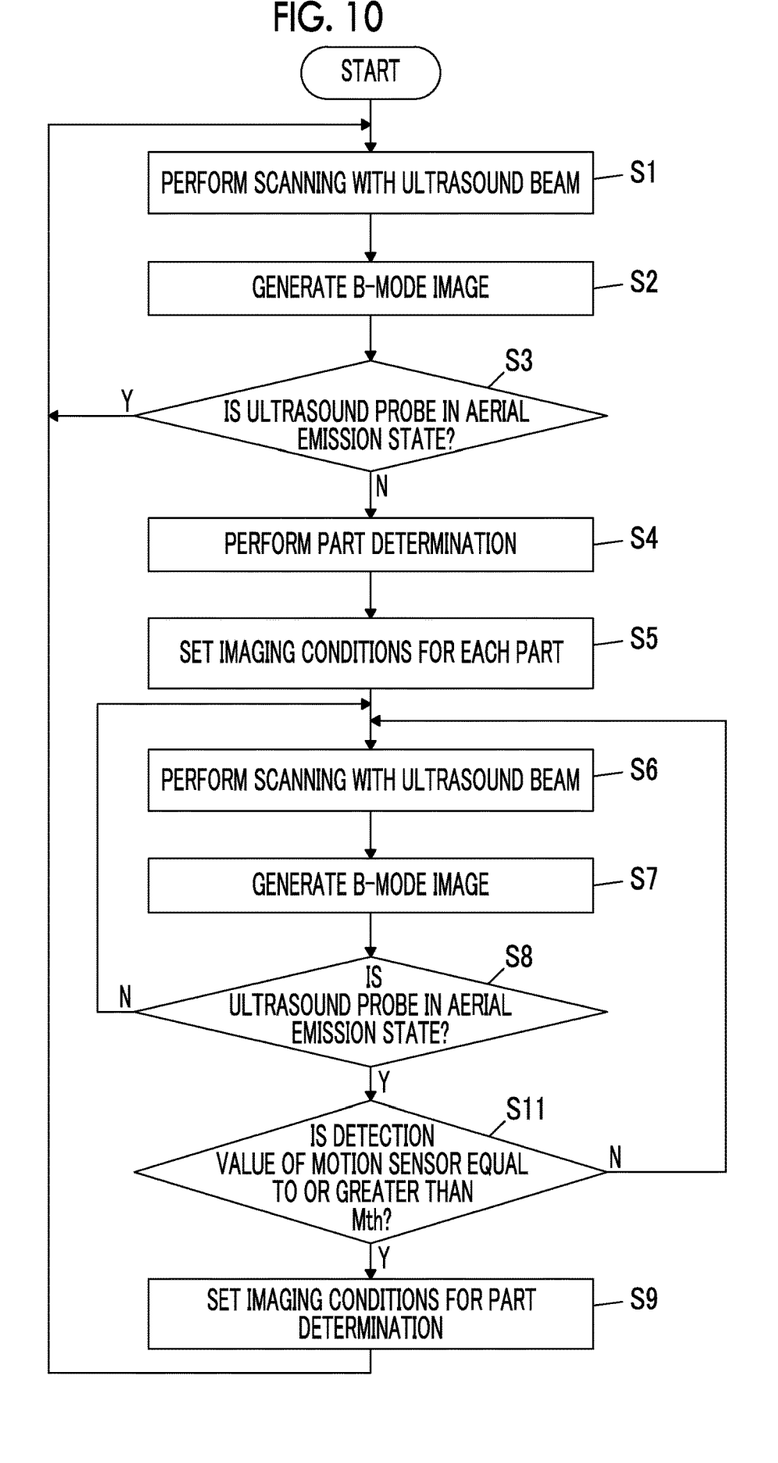
FIG. 10 is a flowchart illustrating the operation of Embodiment 3.

In Embodiment 3, as illustrated in FIG. 10, in a case in which it is determined in Step S11 that the amount of movement of the ultrasound probe 1 detected by the motion sensor 1B is equal to or greater than the predetermined threshold value Mth after the probe state determination unit 12 determines that the ultrasound probe 1 has been changed from the contact state with the subject to the aerial emission state in Step S8, the process proceeds to Step S9 and the imaging conditions for part determination are set.

In a case in which the amount of movement of the ultrasound probe 1 is equal to or greater than the threshold value Mth, the apparatus control unit 14 determines that the operator has intentionally separate the ultrasound probe 1 from the body surface of the subject and sets the imaging conditions for part determination. In contrast, in a case in which the amount of movement of the ultrasound probe 1 is less than the threshold value Mth, the apparatus control unit 14 determines that the ultrasound probe 1 has been unintentionally changed to the aerial emission state and the ultrasound probe 1 has been instantaneously separated and lifted from the body surface of the subject while the image of the imaging part is captured and uses the set imaging conditions for each part without any change.

With this configuration, it is possible to reliably recognize that the ultrasound probe 1 has been intentionally changed to the aerial emission state in order to change the imaging part and to set the imaging conditions for part determination.

According to the invention, in a case in which the imaging part is changed, it is possible to obtain an ultrasound image with stable image quality, regardless of the imaging part immediately before the change. Therefore, in a case in which a plurality of imaging parts are sequentially examined in a predetermined order as in a focused assessment with sonography for trauma (FAST) examination in critical care, it is possible to determine the part to be examined with high accuracy.

EXPLANATION OF REFERENCES

1: ultrasound probe
1A: array transducer
1B: motion sensor
2: transmitting/receiving unit
3: image generation unit
4: display control unit
5: display unit
6: transmitting unit
7: receiving unit
8: transmission/reception control unit
9: B-mode processing unit
10: DSC 11: part determination unit
12: probe state determination unit
14, 14A: apparatus control unit
15: imaging condition memory
16: operation unit
17: storage unit
18: amplification unit
19: A/D conversion unit
20: beam former
21: signal processing unit
22: B-mode image
23: regions
24: observation point

What is claimed is:

1. An ultrasound diagnostic apparatus comprising:
an ultrasound probe;
a memory configured to store, in advance, pattern data associated with each of a plurality of imaging parts;
an imaging condition memory that stores, in advance, (1) a plurality of imaging conditions for each part of a plurality of parts which are set for each of the plurality of the imaging parts, and (2) imaging conditions for part determination which are common to the plurality of imaging parts, each part of the plurality of parts being one of a plurality of anatomical structures; and
a processor configured
to transmit and receive an ultrasound beam to and from a subject using the ultrasound probe and converts a received signal output from the ultrasound probe into an image to generate a B-mode image of the subject using (2) the imaging conditions for part determination which are common to the plurality of imaging parts stored in the imaging condition memory;
to determine that the ultrasound probe is in a contact state with the subject in a case a certain anatomical structure is visualized in the B-mode image, and that the ultrasound probe is in an aerial emission state in a case no anatomical structure is visualized in the B-mode image; and
to determine an imaging part of the subject using the B-mode image based on the pattern data stored in the memory, the imaging part being an anatomical part,
wherein the processor generates the B-mode image using (2) the imaging conditions for part determination stored in the imaging condition memory when it is determined that the ultrasound probe has been changed from the contact state with the subject to the aerial emission state, and
wherein the processor selects an imaging condition for each part corresponding to the imaging part of the subject that was determined using the B-mode image from (1) the plurality of imaging conditions for each part stored in the imaging condition memory when it is determined that the part determination has been completed, and generates the B-mode image using the selected imaging condition for each part corresponding to the imaging part of the subject that was determined using the 13-mode image.

2. The ultrasound diagnostic apparatus according to claim 1,
wherein the processor does not perform part determination when it is determined that the ultrasound probe is in the aerial emission state and performs the part determination when it is determined that the ultrasound probe has been changed from the aerial emission state to the contact state with the subject.

3. The ultrasound diagnostic apparatus according to claim 1,
wherein the processor gradually changes the imaging conditions from (2) the imaging conditions for part determination to (1) the selected imaging condition for each part when the part determination has been completed.

4. The ultrasound diagnostic apparatus according to claim 1,
wherein the processor generates the B-mode image using (2) the imaging conditions for part determination when it is determined that the ultrasound probe has been changed from the contact state with the subject to the aerial emission state and that the ultrasound probe is maintained in the aerial emission state for a predetermined set number of frames.

5. The ultrasound diagnostic apparatus according to claim 2,
wherein the processor generates the B-mode image using (2) the imaging conditions for part determination when it is determined that the ultrasound probe has been changed from the contact state with the subject to the aerial emission state and that the ultrasound probe is maintained in the aerial emission state for a predetermined set number of frames.

6. The ultrasound diagnostic apparatus according to claim 1,
wherein the ultrasound probe includes a motion sensor that detects an amount of movement of the ultrasound probe, and
the processor generates the B-mode image using (2) the imaging conditions for part determination when it is determined that the ultrasound probe has been changed from the contact state with the subject to the aerial emission state and the amount of movement of the ultrasound probe detected by the motion sensor is equal to or greater than a predetermined threshold value.

7. The ultrasound diagnostic apparatus according to claim 2,
wherein the ultrasound probe includes a motion sensor that detects an amount of movement of the ultrasound probe, and
the processor generates the B-mode image using (2) the imaging conditions for part determination when it is determined that the ultrasound probe has been changed from the contact state with the subject to the aerial emission state and the amount of movement of the ultrasound probe detected by the motion sensor is equal to or greater than a predetermined threshold value.

8. The ultrasound diagnostic apparatus according to claim 1,
wherein the processor transmits and receives the ultrasound beam according to ultrasound beam scanning conditions and generates the B-mode image from the received signal according to B-mode image generation conditions, and
the imaging conditions include the ultrasound beam scanning conditions and the B-mode image generation conditions.

9. The ultrasound diagnostic apparatus according to claim 2,
wherein the processor transmits and receives the ultrasound beam according to ultrasound beam scanning conditions and generates the B-mode image from the received signal according to B-mode image generation conditions, and the imaging conditions include the ultrasound beam scanning conditions and the B-mode image generation conditions.

10. A method for controlling an ultrasound diagnostic apparatus including an ultrasound probe, the method comprising:
- a step of storing in a memory, in advance, pattern data associated with each of a plurality of imaging parts;
- a step of storing in an imaging condition memory, in advance, (1) a plurality of imaging conditions for each part of a plurality of parts which are set for each of the plurality of the imaging parts, and (2) imaging conditions for part determination which are common to the plurality of imaging parts, each part of the plurality of parts being one of a plurality of anatomical structures;
- a step of transmitting and receiving an ultrasound beam to and from a subject using the ultrasound probe and converting a received signal output from the ultrasound probe into an image to generate a B-mode image of the subject using (2) the imaging conditions for part determination which are common to the plurality of imaging parts stored in the imaging condition memory;
- a step of determining that the ultrasound probe is in a contact state with the subject in a case a certain anatomical structure is visualized in the B-mode image, and that the ultrasound probe is in an aerial emission state in a case no anatomical structure is visualized in the B-mode image;
- a step of determining an imaging part of the subject using the B-mode image based on the pattern data stored in the memory, the imaging part being an anatomical part:
- wherein the B-mode image is generated when it is determined that the ultrasound probe has been changed from the contact state with the subject to the aerial emission state using (2) the imaging conditions for part determination stored in the imaging condition memory, and
- wherein an imaging condition for each part corresponding to the imaging part of the subject that was determined using the B-mode image from (1) the plurality of imaging conditions for each part is selected from the imaging condition memory when it is determined that the part determination has been completed, and the B-mode image is generated using the selected imaging condition for each part corresponding to the imaging part of the subject that was determined using the B-mode image.

11. The method for controlling an ultrasound diagnostic apparatus according to claim 10,
wherein determination of the imaging part is not performed when it is determined that the ultrasound probe is in the aerial emission state and the determination of the imaging part is performed when it is determined that the ultrasound probe has been changed from the aerial emission state to the contact state with the subject.

12. The method for controlling an ultrasound diagnostic apparatus according to claim 10,
wherein the imaging conditions are gradually changed from (2) the imaging conditions for part determination to (1) the selected imaging condition for each part in a case in which the part determination has been completed.

13. The method for controlling an ultrasound diagnostic apparatus according to claim 10,
wherein the B-mode image is generated using (2) the imaging conditions for part determination when it is determined that the ultrasound probe has been changed from the contact state with the subject to the aerial emission state and that the ultrasound probe is maintained in the aerial emission state for a predetermined set number of frames.

14. The method for controlling an ultrasound diagnostic apparatus according to claim 11,
wherein the B-mode image is generated using (2) the imaging conditions for part determination when it is determined that the ultrasound probe has been changed from the contact state with the subject to the aerial emission state and that the ultrasound probe is maintained in the aerial emission state for a predetermined set number of frames.

15. The method for controlling an ultrasound diagnostic apparatus according to claim 10,
wherein an amount of movement of the ultrasound probe is detected, and
the B-mode image is generated using (2) the imaging conditions for part determination when it is determined that the ultrasound probe has been changed from the contact state with the subject to the aerial emission state and the amount of movement of the ultrasound probe detected is equal to or greater than a predetermined threshold value.

16. The method for controlling an ultrasound diagnostic apparatus according to claim 11,
wherein an amount of movement of the ultrasound probe is detected, and
the B-mode image is generated using (2) the imaging conditions for part determination when it is determined that the ultrasound probe has been changed from the contact state with the subject to the aerial emission state and the amount of movement of the ultrasound probe detected is equal to or greater than a predetermined threshold value.

17. The method for controlling an ultrasound diagnostic apparatus according to claim 10,
wherein the imaging conditions include ultrasound beam scanning conditions used to transmit and receive the ultrasound beam and B-mode image generation conditions used to generate the B-mode image from the received signal.

18. The method for controlling an ultrasound diagnostic apparatus according to claim 11,
wherein the imaging conditions include ultrasound beam scanning conditions used to transmit and receive the ultrasound beam and B-mode image generation conditions used to generate the B-mode image from the received signal.

* * * * *